United States Patent [19]

Jung et al.

[11] Patent Number: 4,906,568
[45] Date of Patent: Mar. 6, 1990

[54] PROCESS FOR ISOLATION OF CARNITINEHYDROLYASE AND AN EFFECTOR FROM ENTEROBACTERIACEAE AND USE THEREOF TO PREPARE CARNITINE

[75] Inventors: Heinrich Jung; Kirsten Jung, both of Wolfen; Hans-Peter Kleber, Leipzig, all of German Democratic Rep.

[73] Assignee: Sigma Tau Industrie Farmaceutiche Riunite S.p.A., Rome, Italy

[21] Appl. No.: 261,858

[22] Filed: Oct. 25, 1988

[30] Foreign Application Priority Data

Oct. 26, 1987 [DD] German Democratic Rep. .... 308242
Oct. 26, 1987 [DD] German Democratic Rep. .... 308243

[51] Int. Cl.$^4$ .............................................. C12P 13/00
[52] U.S. Cl. .................................... 435/128; 435/136; 435/280
[58] Field of Search ................ 435/135, 136, 146, 128

[56] References Cited

U.S. PATENT DOCUMENTS 4,650,759 3/1987 Yokozeki et al. .................... 435/128

FOREIGN PATENT DOCUMENTS 61-67494 7/1986 Japan.

OTHER PUBLICATIONS

Fukui et al—Chem. Abst. vol. 105 (1986) p. 132142U.

Primary Examiner—Sam Rosen
Attorney, Agent, or Firm—Wegner & Bretschneider

[57] ABSTRACT

An enzyme carnitinehydrolyase is isolated from microorganisms belonging to the family Enterobacteriaceae, particularly *Escherichia coli, Proteus vulgarius, Proteus mirabilis, Citrobacter freundii, Salmonella typhimurium, Salmonella anatum, e Salmonella cottbus*, following anaerobic cultivation of the microorganisms in the presence of D,L-carnitine and/or crotonobetaine, by cell disruption and chromatography of the resulting protein extract. The enzyme, upon immobilization and activation by an effector which is also obtained from the protein extract following enzyme isolation, is used for stereoselectively hydrating crotonobetaine into L(−)-carnitine by contacting a solution of crotonobetaine or crotonobetaine derivatives with carnitinehydrolyase in the presence of the effector.

13 Claims, No Drawings

PROCESS FOR ISOLATION OF CARNITINEHYDROLYASE AND AN EFFECTOR FROM ENTEROBACTERIACEAE AND USE THEREOF TO PREPARE CARNITINE

The present invention relates to a process for isolating from culture of strains belonging to the family Enterobacteriaceae an enzyme (hereinafter "carnitinehydrolyase") which immobilized and activated by an effector (hereinafter: "effector F") which is also obtained from the above cultures following enzyme isolation, is capable to catalyze the stereospecific hydration of the achiral precursor crotonobetaine and crotonobetaine derivatives selected from the group consisting of crotonobetaine salts, crotonobetaine nitrile and esters and amides of crotonobetaine, said hydration processing according to the reaction scheme:

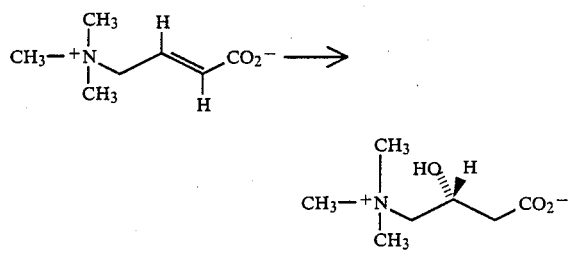

As is well known, carnitine contains a center of asymmetry and therefore, carnitine exists in two stereoisomeric forms, the D and the L forms.

L-carnitine is normally present in the body where it functions to carry activated long-chain free fatty acids through the mitochondrial membrane. Since the mitochondrial membrane is impermeable to acyl CoA derivatives, long-chain free fatty acids can enter only when esterification with L-carnitine has taken place.

While it has been established that the laevorotatory isomer (L-carnitine) exclusively is the biological form (D-carnitine has never been detected so far in mammalian tissues), the D,L-carnitine racemate has been used for a number of years for different therapeutical indications.

Recently, however, there has been an increasing emphasis on the importance of utilizing exclusively the carnitine laevoroatatory isomer. It has, in fact, been shown that D-carnitine is a competitive inhibitor of carnitine-linked enzymes such as carnitine acetyl transferase (CAT) and carnitine palmityl transferase (PTC). For instance, it has been shown that D-carnitine can deplete the L-carnitine level of myocardium and skeleted muscle. Consequently, it is essential that L-carnitine exclusively be administered to patients under medical treatment for heart diseases or regular haemodialytic treatment or lowering the blood lipids.

Several chemical processes have been proposed for producing carnitine on an industrial scale. These processes are not stereospecific and therefore, unavoidably lead to a racemic mixture of the D and L isomers. Consequently, resolution methods have to be employed to obtain the separate optical antipodes from the racemate.

These processes are complex and expensive and in any case lead to the production of as much D-carnitine (which is a cumbersome waste product) as L-carnitine is produced.

Recently, several microbiological processes have been proposed for stereoselectively producing L(—)-carnitine starting from achiral precursors. Some of these processes are based on the stereospecific hydration of crotonobetaine into L(—)-carnitine according to the previously illustrated reaction scheme. These processes substantially differ from each other because of the specific microbial strain utilized to furnish the enzyme which catalyzes the reaction, although generally all the strains belong to the family Enterobacteriaceae. These processes are, for example, disclosed in the patent applications EP 121,444 (Hamari), EP 122,799 (Ajinomoto), DDR patent 221,905 (Karl Marx University). In the Japanese patent application 61/234,788 (Seitetsu) and in the patent applications EP 158,194 and 195,944 (Lonza)

All these processes present serious drawbacks that make it difficult, if not at all impossible, to carry them out on an industrial scale. These drawbacks mainly consist in the high cost of culture media which must be complex media enriched with vitamins and other expensive nutrients, the low conversion ability of most of the disclosed strains, the low concentration of crotonobetaine in the reaction mixture, the taking place of concurrent side-reactions such as the conversion of crotonobetaine into gamma-butyrobetaine which diverts part of the already scanty substrate from the sought conversion into L(—)-carnitine or the conversion of some of the produced L(—)-carnitine into further metabolites when the microorganisms turn to L(—)-carnitine as a C-source. Indeed, the utilized microrganisms not only possess the desired enzyme that carries out the stereoselective hydration of crotonobetaine into L(—)-carnitine, but also further enzymes which catalyze reactions competing with the industrially relevant reaction.

It is therefore, apparent that it would be desirable to selectively isolate from the foregoing microorganisms the enzyme capable to stereospecifically hydrate crotonobetaine into L(—)-carnitine, separating it from those enzymes which catalyze reactions other than the one which is industrially relevant, particularly from the reductase catalyzing the conversion of crotonobetaine into gamma-butyrobetaine. It could then be possible to use this enzyme, suitably purified, enriched and immobilized, in the L(—)-carnitine synthesis.

It has now been found that it is possible to isolate in good yields from some strains of Enterobacteriaceae and particularly from

| | |
|---|---|
| *Escherichia coli,* preferably | E. coli 044 K74 |
| | E. coli 055 K59 |
| | E. coli 0111 K58 |
| | E. coli 0114 K90 |
| *Proteus vulgaris,* preferably | P. vulgaris |
| | P. mirabillis |
| *Citrobacter,* preferably | C. freundii |
| *Salmonella,* preferably | S. typhimurium LT$_2$ |
| | S. anatum |
| | S. cottbus |

The enzyme capable of stereoselectively hydrating crotonobetaine into L(—)-carnitine. This enzyme will be referred to as carnitinehydrolyase. More specifically, it has been found that from the foregoing strains it is possible to isolate both the carnitinehydrolyase (which is inactive per se) and an effector that, in the presence of the enzyme, is capable to restore the activity thereof.

According to the present invention, the handling of the stock solution preferably takes place on a nutritive medium or broth containing agar-agar (II) (20 g/l). The slant tubes are incubated at 37° C. for 8 hours, and stored at 4° C. The stock solutions are cultivated in a culture submersed in a complex nutritive medium which means a medium to which at least glycerol (1 to 50 mmol/l, preferably 20 mmol/l), fumaric acid (1 to 50 mmol/l, preferably 20 mmol/l) and D,L-carnitine (1 to 100 mmol/l, preferably 10 mmol/l) have been added, or one of the salts thereof, so as to induce the carnitine hydrolysis to a sufficient extent.

After 6 to 24 (preferably 8 to 15) hours of incubation under anaerobic conditions at a temperature of 20° to 45° C. (preferably 37° C.), the cells are harvested by means of centrifugation, and after washing with a phosphate buffer solution they are standardized by mechanical treatment, e.g., by frictional treatment in the presence of Alcoa, or in an ultrasonic process. The raw protein extract is collected in a phosphate buffer solution and centrifuged so as to be separated from the Alcoa and the whole cells which are still present. Then ammonium sulfate is added successively to the raw protein extract up to a saturation in the concentration range between 25 and 40%. After centrifugation the enzyme is isolated from the supernatant by way of chromatographic separation on phenyl sephar, hydroxylapatite, DEAE sephar or DEAE-cellulose ester, or by way of gel filtration through Sephadex G 100.

The thus obtained enzyme is inactivated. For its reactivation an effector (F) is required which is also produced from the protein extract after the extraction and isolation of the carnitinehydrolyase. After the chromatographic stage, the eluate containing the effector actually undergoes ultrafiltration (in an Amicon ultrafiltration equipment with YM 5 membrane) so as to separate it from the remaining proteins. The addition of the effector F to the isolated enzyme immediately results in the activation of the carnitinehydrolyase. With the aforedescribed conditions, the enrichment of the enzyme is achieved up to a specific activity level of 5 U/mg approximately. The enzyme produced in accordance with the invention can be stored at 4° C. for several months.

Alternatively it is possible to add the effector F to the solution containing the crotonobetaine in order to activate the carnitinehydrolyase.

This method of carnitinehydrolysis producing the immobilized hydrolyase can already be applied in a discontinuous or continous form for synthesizing the L(−)-carnitine when the latter is brought into contact with a solution containing approximately 1 to 10 mmol of crotonobetaine/liter, to which is added the effector F. After the lapse of a certain incubation period (5 to 30 min.) and with a flow rate of 1 to 100 ml/h, the L(−)-carnitine is produced from the crotonobetaine (Tables 2, 3, 4). The non transformed crotonobetaine can be treated in another reaction cycle after the separation of the L(−)-carnitine produced; the effector F may also be re-used by way of analogy. To increase the percentage of carnitinehydrolyase per ml of phenyl sephar (Table 5) and to increase the stability of the enzyme, the carnitinehydrolyase can be concentrated in subsequent purification steps (chromatographic separation on phenyl sephar, hydroxylapatite and DEAE sephar). To the concentrated product is added ammonium sulfate up to a saturation level of 25 to 40%, whereupon immobilization takes place on phenyl sephar 4B. The thus immobilized enzyme is charged into a column and may be employed in the continuous synthesis of L(−)-carnitine from crotonobetaine.

The production of L(−)-carnitine from crotonobetaine by way of carnitinehydrolysis producing an immobilized hydrolyase, is a process which depends on both temperature and pH level. Good conversion reactions are achieved at a temperature between 25° and 40° C., preferably at 37° C., and at a pH value between 6.0 and 9.0, preferably 7.5.

In the following, several examples of the isolation of the carnitinehydrolyase and the production of the effector F, as well as the use of the immobilized enzyme activated by the transformation of the crotonobetaine into L(−)-carnitine will be described.

EXAMPLE 1

The cultivation of *Eschrichia coli* 044 K74 is performed sumersed in a 10-liter vessel, which is filled to the top with a medium which contains carnitine (pancreatic peptone 20 g/l, NaCl 5 g/l, glycerol 10 ml/l, fumaric acid 2 g/l, D,L-carnitine HCl 3 g/l). It is adjusted to a pH of 7.5 with NaOH. Vaccination is performed with 500 ml of an aerobic preculture in complex medium (pancreatic peptone 20 g/l, NaCl 5 g/l) from the exponential growth phase. The primary vaccination density amounts to $$\Delta E^{1cm}_{600\ nm} \sim 0.08.$$

The culture vessel is sealed to be air-tight and is left to stand for 8 hours at 37° C. In order to isolate the enzyme, the bacteria are harvested after the termination of the incubation by means of centrifugation for 15 min at 6000 xg and 4° C. and are then washed twice with 0.067M phosphate buffer pH 7.5. The cells are decomposed by Alcoa (10 minutes crushing at 4° C.). The protein is extracted with 0.05M phosphate buffer (pH 7.5) and by means of centrifugation for 30 min. at 15,000 xg and 4° C. is separated from Alcoa and from non-decomposed cells. To the protein raw extracted which is obtained in this way, ammonium sulphate is added up to a saturation concentration of 25%. After 30 minutes stirring at 4° C., the raw protein extract is centrifuged at 15,000 xg for 30 minutes. The supernatant obtained thereby is applied on a phenylsepharose column (2×15 cm), which is equilibrated with a 25% ammonium sulphate solution in 0.05M phosphate buffer (pH 7.5). Subsequently the column is washed with 150 ml of the 25% ammonium sulphate solution. All the fractions obtained in this process, which have a $$E^{1cm}_{280\ nm} > 30,$$

are com bined and the solution is freed from protein by means of ultrafiltration (Amicon ultrafiltration cell, membrane YM 5). The solution thus obtained is described below as solution F. The carnitinehydrolyase is eluted with a 15% ammonium sulphate solution from the phenylsepharose column. The speed of elution amounts to 50 ml/hour. 3.5 ml fractions are collected. The active fractions are combined and are dialysed for 12 hours against 5 l 0.01M phosphate buffer (pH 7.5). The dialysed protein solution is then applied on a hydroxylapatite column (1.5×10 cm) which is equilibrated with 0.01M phosphate buffer (pH 7.5). After washing the column with phosphate buffer, the enzyme is eluted from the column with 0.03M phosphate buffer, pH 7.5, and the active fractions are combined. The speed of elution amounts to 20 ml/hour. 3 ml fractions are collected. The enzyme solution thus obtained is applied on a column (0.9×10 cm), which is filled with DEAE sepharose CL 6B. This column is equilibrated with 0.03M phosphate buffer, pH 7.5, and is also washed after the application of the protein solution with 50 ml of this buffer. The elution of the enzyme is carried out by means of a 200 ml gradient of 0.03M to 0.30M phosphate buffer pH 7.5. The speed of elution amounts to 20 ml/hour. 2.5 ml fractions are collected. The active fractions are combined and are concentrated by means of ultrafiltration (Amicon ultrafiltration cell, membrane YM 5) to 2 ml. The concentrated protein solution is applied on a sephadex G 100 column (1.5×45 cm) which is equilibrated with 0.05M phosphate buffer pH 7.5. The speed of elution amounts to 12 ml/hour. 2 ml fractions are collected. The combined active fractions are concentrated by means of ultrafiltration (Amicon ultrafiltration cell, membrane YM 5) to 5 ml. In order to activate the prepared enzyme, solution F is added (50% v/v) to the respective reaction batch. The carnitinehydrolyase thus obtained is enriched up to a specific activity of 4.95 U/mg. The steps for preparation are summarized in Table 1.

TABLE 1

Purification of the carnitinehydrolyase from Escherichia coli 044 K74

| Purification Stage | Total Protein (mg) | Spec. activity (U/mg) | Total activity (U) | Yield (%) | Enrichment |
|---|---|---|---|---|---|
| Raw extract | 4140 | 0.050 | 207 | 100 | — |
| Supernatant after saturation with 25% (NH$_4$)$_2$SO$_4$ | 3957 | 0.047 | 186 | 90 | 1 |
| Phenylsepharose | 1010 | 0.100 | 101 | 49 | 2 |
| Hydroxylapatite | 162 | 0.450 | 73 | 35 | 9 |
| DEAE sepharose | 46 | 1.250 | 58 | 29 | 25 |
| Gelfiltration | 11 | 4.75 | 52 | 25 | 95 |

EXAMPLE 2

The process is carried out as described in Example 1 above, but the strain Proteus vulgaris is cultivated. After isolation and enrichment of the enzyme, carnitinehydrolyase is obtained with a specific activity of 5.2 U/mg.

EXAMPLE 3

The process is carried out as described in Example 1, but the strain Citrobacter freundii is cultivated. After isolation and enrichment, carnitinehydrolyase is obtained with a specific activity of 4.3 U/mg.

EXAMPLE 4

The cultivation of Escherichia coli 044 K74 is performed submersed in a 5 liter vessel, which is filled to the top with a carnitine-containing complex medium (20 g pancreatic peptone, 5 g NaCl, and 3 g D,L-carnitine HCl pro 1 aqua dist.). It is adjusted to a pH of 7.5 by means of NaOH. Vaccination is carried out with 250 ml of an aerobic preculture (E=1.8 at λ=600 nm, d=1 cm) when using the named complex medium without carnitine additive. The culture vessel is sealed to be air-tight and incubation is carried out for 8 hours at 37° C. Then the bacteria are harvested by centrifugation for 15 minutes at 6000 xg and 4° C. and are washed twice over with phosphate buffer (0.067M, pH 7.5). The cells are decomposed with Alcoa (10 minutes crushing at 4° C.). The protein is extracted by means of 40 ml phosphate buffer (0.05M, pH 7.5) and are separated by centrifugation for 30 minutes at 15,000 xg and 4° C. from Alcoa and from non-decomposed cells. To the extract thus obtained 17 ml of a 100% (NH$_4$)$_2$SO$_4$ solution (pH 7.5) are added drop by drop over a period of 20 minutes while stirring (final concentration of (NH$_4$)$_2$SO$_4$ is 30%). After stirring for a further 15 minutes, the extract is centrifuged at 30 minutes at 15,000 xg and at 4° C. For the immobilization of the carnitinehydrolyase, 15 ml of well precipitated phenylsepharose are employed, which were previously washed with 200 ml of a 30% (NH$_4$)$_2$SO$_4$ solution in phosphate buffer (0.05M, pH 7.5). The protein extract is mixed with the phenylsepharose and is stirred carefully for 15 minutes. Non-bonded material is separated via a glass frit G3 from the phenylsepharose. The latter is subsequently mixed with 60 ml of a 30% (NH$_4$)$_2$SO$_4$ solution in phosphate buffer (0.05M, pH 7.5). The filtrate is combined with the washing buffer and is freed from protein by means of Amiconfiltration, membrane YM 5.

The solution which is prepared in this manner is described in the following as solution F. In this way, 5 U carnitinehydrolyase per mg phenylsepharose are immobilized. For the synthesis of L(−)-carnitine from crotonobetaine the immobilized enzyme is brought into contact with a solution of 5 mmoli/l crotonobetaine in F. The incubation is carried out while stirring at 37° C. After varying incubation times, the synthesized L(−)-carnitine is separated with a glass plug G3 from the gel. The formation of L(−)-carnitine, dependent on time elapsed, is shown in Table 2.

TABLE 2

Time dependence of L(−)-carnitine from crotonobetaine by immobilized carnitinehydrolyase.

| Incubation Time minutes | μmol/ml | Synthesis of L(−)-carnitine $\frac{(L-)\text{-carnitine (μmol)}}{\text{crotonobetaine (μmol)}} \cdot 10^2$ |
|---|---|---|
| 1 | 0,80 | 16 |
| 3 | 1,45 | 29 |
| 5 | 2,25 | 43 |
| 10 | 2,70 | 54 |
| 20 | 3,25 | 65 |
| 30 | 3,35 | 67 |

EXAMPLE 5

The synthesis of L(−)-carnitine by means of a carnitinehydrolyase which is immobilized in accordance with example 4 on phenylsepharose is carried out with differing concentrations of crotonobetaine. For this purpose the immobilized enzyme is incubated with the respective crotonobetaine solution in solution F for 30 minutes at 37° C. while being stirred. After the incubation is completed, the L(−)-carnitine-containing solution is separated by means of a glass plug G3 from the gel (Table 3).

TABLE 3

Formation of L(−)-carnitine at varying concentrations of crotonobetaine

| Crotonobetine μmol/ml | μmol/ml | Synthesis of L(−)-carnitine $\frac{(L-)\text{-carnitine (μmol)}}{\text{crotonobetaine (μmol)}} \cdot 10^2$ |
|---|---|---|
| 0.5 | 0.3 | 60 |
| 1.0 | 0.68 | 68 |
| 5.0 | 3.2 | 64 |

TABLE 3-continued

Formation of L(−)-carnitine at varying concentrations of crotonobetaine

| Crotonobetine μmol/ml | Crotonobetaine μmol/ml | Synthesis of L(−)-carnitine $\frac{L(-)\text{-carnitine } (\mu mol)}{\text{crotonobetaine } (\mu mol)} \cdot 10^2$ |
|---|---|---|
| 10.0 | 6.5 | 65 |
| 20.0 | 10.0 | 50 |

EXAMPLE 6

In accordance with Example 4 carnitinehydrolyase which is immobilized on phenylsepharose is filled in a column (1×6 cm). By means of a peristaltic pump crotonobetaine which is dissolved in solution F is continously pumped from a storage vessel over the column. The columns as well as the storage vessel are kept at 37° C. The synthesis of L(−)-carnitine from crotonobetaine dependent on the flow speed and on the concentration of crotonobetaine is shown in Table 4.

TABLE 4

Continuous formation of L(−)-carnitine from crotonobetaine

| Crotonobetaine μmol/ml | Flow Speed ml/h | Synthesis of L(−)-carnitine | |
|---|---|---|---|
| | | μmol/ml | $\frac{L(-)\text{-carnitine } (\mu mol)}{\text{crotonobetaine } (\mu mol)} \cdot 10^2$ |
| 1 | 20 | 0.4 | 40 |
| | 10 | 0.6 | 60 |
| | 5 | 0.65 | 65 |
| 5 | 20 | 1.5 | 30 |
| | 10 | 2.25 | 45 |
| | 5 | 2.9 | 58 |
| 10 | 20 | 2.4 | 24 |
| | 10 | 4.0 | 40 |
| | 5 | 5.0 | 50 |

EXAMPLE 7

Bacteria of a 10 l culture in accordance with example 4 are cultivated, harvested, and decomposed by means of Alcoa. The extraction of the protein is performed with 100 ml phosphate buffer (0.05M, pH 7.5). The Alcoa as well as the non-decomposed cells are separated by centrifuging for 30 minutes at 15,000 xg and at 4° C. To the supernatant 33.3 ml of a 100% $(NH_4)_2SO_4$ solution are added drop by drop over a period of 30 minutes while stirring. After stirring for 15 minutes, the centrifuging is effected for 30 minutes at 15,000 xg and at 4° C. The supernatant which is obtained in this way is then applied on a phenyl sepharose column (2×15 cm). The column is previously equilibrated with 200 ml of a 25% $(NH_4)_2SO_4$ solution in phosphate buffer (0.05M, pH 7.5). After the application of the protein solution, the column is washed with 100 ml of the equilibration buffer. The eluate is measured at 280 nm using a spectrophotometer. All the fractions which have a Δ E>30 (where d=1 cm) are combined. This solution is freed from protein by means of Amicon filtration (membrane YM 5). The solution free of protein is subsequently described as solution F'. The elution of the carnitinehydrolyase from the phenylsepharose column is effected by a 15% solution of $(NH_4)_2SO_4$ in phosphate buffer (0.05M, pH 7.5). 4 ml fractions are collected. The speed of elution amounts to 50 ml/hour. The combined active fractions are dialysed against 5 l of phosphate buffer (0.01M, pH 7.5) for 12 hours. The dialysed protein solution is applied on a hydroxylapatite column (1.5×7 cm) which is previously equilibrated with 100 ml phosphate buffer (0.01M, pH 7.5). After washing with 50 ml phosphate buffer (0.01M, pH 7.5) the carnitinehydrolyase is eluted by means of phosphate buffer (0.03M, pH 7.5). 3 ml fractions are collected. The speed of elution amounts to 20 ml/hour.

The combined active fractions are subsequently applied on a DEAE sepharose column (0.9×10 cm). This column is washed with 50 ml phosphate buffer (0.03M, pH 7.5). The elution of the carnitinehydrolyase is carried out using a linear phosphate gradient (0.03 to 0.30 mol/l phosphate buffer, pH 7.5). The active fractions are combined and are concentrated by means of Amicon filtration (membrane YM 5) to 3 ml. This solution then has 1.3 ml of a 100% ammonium sulphate solution added to it. After 30 minutes of stirring, the solution is mixed with 1 ml of phenylsepharose and is stirred for a further 30 minutes. Subsequently it is washed with 10 ml of a 30% ammonium sulphate solution in phosphate buffer (0.05M, pH 7.5). The phenylsepharose which is prepared in this way contains 40 U immobilized carnitinehydrolyase per ml of the gel. The enzyme bonded on phenylsepharose is filled into a column (0.8×2.0 cm). Crotonobetaine dissolved in solution F' is conducted over this column by means of a peristatic pump at a speed of 3.6 ml/hour. The operating temperature amounts to 37° C. Table 5 shown the synthesis of L(−)-carnitine at different concentrations of crotonobetaine.

TABLE 5

Continuous formation of L(−)-carnitine with purified carnitinehydrolyase.

| Crotonobetaine μmol/ml | Flow Speed ml/h | Synthesis of L(−)-carnitine | |
|---|---|---|---|
| | | μmol/ml | $\frac{L(-)\text{-carnitine } (\mu mol)}{\text{crotonobetaine } (\mu mol)} \cdot 10^2$ |
| 1 | 30 | 0.55 | 55 |
| | 15 | 0.65 | 65 |
| | 5 | 0.63 | 63 |
| 5 | 30 | 2.45 | 49 |
| | 15 | 2.75 | 55 |
| | 5 | 3.00 | 60 |

EXAMPLE 8

The process is carried out as in example 4, but using proteus vulgaris. On incubation of the enzyme isolated from this strain and immobilized on phenylsepharose with a solution of 5 mmol/l crotonobetaine in F, after 30 minutes 3 mmol/l L(−)-carnitine are formed.

EXAMPLE 9

The process is performed as in example 4 using citrobacter freundii. On incubation of the enzyme immobilized on phenyl sepharose and isolated from that strain with a solution of 5 mmol/l crotonobetaine in F, after 30 minutes 2.3 mmol/l L(−)-carnitine are formed.

What is claimed is:

1. A process for microbiologically producing L(−)-carnitine by stereospecific hydration of crotonobetaine and crotonobetaine derivatives, which comprises:
    (a) isolating from strains belonging to the family Enterobacteriaceae an enzyme carnitinehydrolyase per se inactive and an effector which in the presence of the enzyme activates it making it capable of stereoselectively hydrating crotonobetaine into L(−)-carnitine, by (i) cultivating said strains under anaerobic conditions on a complete culture medium containing D,L-carnitine and/or crotonobetaine;

(ii) disrupting the Enterobacteriaceae cells thus obtaining a raw protein extract;

(iii) chromatographying the raw protein extract on a support comprising hydrophobic anionic exchange resins thus achieving the isolation and immobilization of carnitinehydrolyase on the support and producing an eluate which comprises a protein fraction and the effector;

(iv) ultrafiltrating the eluate thus obtaining a filtrate containing the effector and practically free from proteins and carnitinehydrolyase;

(b) contacting a solution of crotonobetaine or crotonobetaine derivatives with carnitinehydrolyase in the presence of the effector thus obtaining L(−)-carnitine; and (c) separating L(−)-carnitine from unreacted crotonobetaine and the effector.

2. The process of claim 1 wherein the strains are selected from the genera *Escherichia, Proteus, Citrobacter* and *Salmonella.*

3. The process of claim 2 wherein the strains are selected from the species:

*Escherichia coli*
*Proteus vulgaris*
*Proteus mirabilis*
*Citrobacter freundii*
*Salmonella typhimurium*
*Salmonella anatum*
*Salmonella cottbus.*

4. The process of claim 3 wherein the *Escherichia coli* strain is selected from:

*Escherichia coli* 044 K74
*Escherichia coli* 055 K59
*Escherichia coli* 0111 K58
*Escherichia coli* 0114 K90

5. The process of claim 1 wherein the support material of step (a) (iii) is selected from phenylsepharose, hydroxyapatite, DEAE-sepharose and DEAE-cellulose.

6. The process of claim 1 wherein before carrying out step (b) the carnitinehydrolyase is enriched.

7. The process of claim 1 wherein the carnitinehydrolyase immobilized on a support is activated by contacting it with an effector-containing solution.

8. The process of claim 1 wherein the carnitinehydrolyase immobilized on a support is activated by contacting it with a solution containing both the effector and crotonobetaine or the crotonobetaine derivative to be converted into L(−)-carnitine.

9. The process according to claim 1 wherein in step (b) a solution comprising from 1 to 10 mmoles of crotonobetaine or crotonobetaine derivative is contacted at 25°–40° C. and pH 6–9 with the carnitinehydrolyase.

10. The process of claim 9 wherein a solution containing 5 mmoles crotonobetaine/liter is fed at 37° C., at a flow rate of 6 ml/hour, at pH 7.5, in the presence of the effector, into a column containing the immobilized carnitinehydrolyase.

11. The process according to claim 1, carried out continuously.

12. The process according to claim 1 wherein the unreacted crotonobetaine is re-cycled following separation from L(−)-carnitine.

13. The process according to claim 1 wherein the crotonobetaine derivative is selected from crotonobetaine salts, crotonobetaine nitrile and esters or amides of crotonobetaine.

* * * * *